United States Patent [19]

Drake et al.

[11] Patent Number: 5,126,306

[45] Date of Patent: Jun. 30, 1992

[54] ALKALI METAL CATALYTIC SLURRY COMPOSITION

[75] Inventors: Charles A. Drake, Nowata; Lori C. Hasselbring, Bartlesville, both of Okla.

[73] Assignee: Phillips Petroleum Company, Bartlesville, Okla.

[21] Appl. No.: 719,417

[22] Filed: Jun. 24, 1991

[51] Int. Cl.$^5$ .................. B01J 23/04; B01J 27/232
[52] U.S. Cl. ............................ 502/174; 502/344; 502/184
[58] Field of Search .................... 502/174, 344, 184

[56] References Cited

U.S. PATENT DOCUMENTS

| | | | |
|---|---|---|---|
| 3,207,812 | 9/1965 | Hambling et al. | 260/683.15 |
| 3,916,019 | 10/1975 | Closson et al. | 260/683.15 E |
| 4,338,096 | 7/1982 | Mayes | 23/230 |
| 4,520,126 | 5/1985 | Kawamoto et al. | 502/184 |
| 4,544,790 | 10/1985 | Drake | 585/516 |
| 4,595,787 | 6/1986 | Drake | 585/516 |
| 4,599,551 | 7/1986 | Wheatley et al. | 322/2 R |
| 4,609,637 | 9/1986 | Drake | 502/174 |
| 4,656,154 | 4/1987 | Drake | 502/185 |
| 4,661,466 | 4/1987 | Drake et al. | 502/184 |
| 4,727,213 | 2/1988 | Drake et al. | 585/511 |

Primary Examiner—W. J. Shine
Assistant Examiner—Douglas J. McGinty
Attorney, Agent, or Firm—Richmond, Phillips, Hitchcock & Umphlett

[57] ABSTRACT

A catalyst system composition and a dimerization process utilizing said catalyst system composition are disclosed. The catalyst system composition comprises at least one elemental alkali metal combined with at least one particulate solid, and optionally a promoter, to form a slurry. This catalyst system is contacted with at least one olefin in order to produce a dimerized product.

14 Claims, No Drawings

ALKALI METAL CATALYTIC SLURRY COMPOSITION

BACKGROUND OF THE INVENTION

This invention relates to catalysts and dimerization processes utilizing catalysts. More particularly, this invention relates to catalyst systems comprising liquid alkali metals and particulates, and dimerization processes catalyzed thereby.

Catalyst systems comprising one or more elemental alkali metals deposited and/or supported on an alkali metal carbonate support have been disclosed in the art for use in dimerization reactions. The prior art teaches that a necessary step in the process of preparing these dimerization catalyst systems is deposition of one or more alkali metals on a support. However, elimination of a time-consuming catalyst preparation step, involving elemental alkali metal deposition onto a support, would be a significant advance in the art.

SUMMARY OF THE INVENTION

An object of this invention is to provide an improved process of preparing a catalyst system for a dimerization process.

Another object of this invention is to eliminate a process step of depositing one or more elemental alkali metals on a support in the preparation of a catalyst system for a dimerization process, while maintaining sufficient catalytic activity, product selectivity, and isomer ratio.

Still another object of this invention is to reduce the time and cost required to prepare a catalyst system for a dimerization process.

Another object of this invention is to provide an improved catalyst system, which is useful for dimerization processes.

Still another object of this invention is to provide a novel dimerization process.

Other objects and advantages will be apparent from the specification and the claims.

In accordance with the present invention, a catalyst system, comprising a slurry of at least one elemental alkali metal and particulate solids, wherein said slurry partially suspends said particulate solids, is provided. In accordance with another embodiment of this invention, the novel catalyst system, is contacted with one or more olefins to produce a dimerized product. This catalyst system eliminates the preparation step of depositing an elemental alkali metal upon the surface of a support material, thereby lowering catalyst system preparation time. This reduction in preparation time lowers catalyst system production costs.

According to one embodiment of the invention, a catalyst system comprising a slurry of a particulate potassium carbonate and a eutectic liquid mixture of sodium and potassium is disclosed. Another embodiment of this invention relates to a process of dimerizing propylene to produce 4-methyl-1-pentene catalyzed by such a slurry.

DESCRIPTION OF THE PREFERRED EMBODIMENTS

Particulate Solids

A particulate solid, as used in this disclosure, is typically a solid material under the dimerization reaction conditions hereinafter disclosed, which is usually inert but can contribute to catalytic activity. In addition, the term "alkali metal carbonate", as used in this disclosure, includes both alkali metal carbonates and alkali metal bicarbonates. Furthermore, a slurry, as used in this disclosure, is a liquid mixture containing suspended, or partially suspended, insolubles, such as, for example, particulate solids.

Particulate solids utilized in the present invention can be formed by any method known in the art. Thus, commercially available alkali metal carbonates in the form of powder, granules, pellets, or any other form can be utilized as particulate solids. These particulate solids can be used directly from the manufacturer or supplier, without further preparation. In addition, other suitable particulate solids include, but are not limited to, glass beads, particulate graphite, and particulate stainless steel. Optionally, one or more of the desired promoting materials, as discussed more fully below, can be added to the catalyst system.

Exemplary alkali metal carbonates include carbonates of lithium, sodium, potassium, rubidium, cesium, and mixtures thereof. Potassium carbonate, i.e., $K_2CO_3$ is the most preferred due to ease of use and good compatibility with the preferred elemental alkali metals.

In some circumstances, a large particle size and/or more rugged form of particulate solid is desired. For example, this form of particulate solid can be preferable in fixed bed reactors, especially those with relatively large volumes. One particular technique for such particulate solid preparation is to form a thick paste comprising alkali metal carbonate and water; alkali metal carbonate, water, and alcohol; or alkali metal carbonate, water, and water soluble ketone. The thick paste can be extruded, pelletized, pilled, or tabletted into appropriate sizes. The resultant material is then oven dried under conditions of time and temperature such that substantially all liquid is driven off. These types of particulate solids will be referred to as "wet process" alkali metal carbonate particulate solids.

The wet process using alcohol and water is disclosed in Ewert et al, U.S. Pat. No. 4,810,688, herein incorporated by reference. Alcohols suitable for use in preparation of "wet process" particulate solids are straight chain and branched aliphatic alcohols having from about 1 to about 7 carbon atoms. The "wet process" using water soluble ketone and water is disclosed in Drake, U.S. Pat. No. 4,895,819, herein incorporated by reference. Water soluble ketones suitable for use in preparation of "wet process" particulate solids are straight chain and branched water soluble ketones having from about 3 to about 7 carbon atoms.

In accordance with another technique for particulate solid preparation, at least one alkali metal carbonate is pelletized with at least one carbonaceous compound. The pelletized particulate solid, either as pellets or as smaller crushed particles, is then heated in an oxygen-containing atmosphere under conditions suitable to oxidize in the range of about 10 to 90 weight percent of the carbonaceous compound. As a result of this partial oxidation of the pelletized support, the concentration of carbonaceous compound remaining on the surface of the particulate solid is substantially less than the concentration of carbonaceous compound remaining on the interior portions of the particulate solid. Particulate solids prepared in this manner will be referred to as "carbon containing" alkali metal carbonate particulate solids.

The term "carbonaceous compound" is intended to include various forms of the elemental carbon. Examples include, but are not limited to, carbon black, charcoal, coconut charcoal, amorphous graphite, and crystallite graphite.

In accordance with another technique for the particulate solid preparation, alkali metal carbonate can be mixed with a non-acidic inorganic oxide and/or a finely divided stainless steel. The mixture is heated to at least 950° C., then cooled, and finally, if desired, broken into pieces or fractionated to a desired particle size. Particulate solids prepared in this manner will be referred to as "melt process" alkali metal carbonate particulate solids.

Suitable non-acidic inorganic oxides include, but are not limited to, alumina, silica, silica-alumina, magnesia-titania, thoria, magnesia, titania, zirconia, and mixtures of two or more thereof. Stainless steel as used herein is intended to cover broadly those alloys of iron which are relatively inert to the reaction conditions employed for olefin dimerization.

Preferably, the particulate solids used in accordance with this invention are not larger than about 0.25 inch diameter. Larger particulate solids can diminish catalytic activity and/or impede flow.

Once a particulate solid is formed, preferably the particulate solid is calcined in an oxygen-containing atmosphere at a temperature in the range of about 80° to about 350° C., preferably about 200° to about 300° C., for a time of at least 2 hours. Times in excess of about 20 hours generally impart no additional beneficial effect. Therefore, times in the range of about 2 to 20 hours are useful. Upon completion of calcination, the particulate solid can be stored in a dry atmosphere. Preferably, the particulate solid is stored under a dry, oxygen-free atmosphere until needed for further treatment.

Catalysts and Promoters

Catalyst systems employed in the practice of this invention comprise one of the particulate solids described above, at least one elemental alkali metal, and optionally one or more of the following promoters:
graphite,
elemental copper,
elemental cobalt,
finely divided stainless steel, and
finely divided glass.
However, the catalyst systems of this invention may contain additional components which do not adversely affect the catalyst performance, such as pigments, dyes, processing aids, inert fillers, binders and the like.

The elemental alkali metals, also referred to as alkali metals, contemplated to be within the scope of the invention include the elemental forms of lithium, sodium, potassium, rubidium, cesium, and mixtures thereof. The more preferred alkali metals include a mixture of sodium and potassium or pure potassium, although pure sodium is within the scope of this invention. Sodium and potassium are most preferred because these elements provide the highest catalytic activity.

The preferred composition of the alkali metal mixture contains at least about 60 percent potassium and up to about 40 percent sodium by weight, based on the total mixture weight. The most preferred composition comprises about 76 to 80 percent potassium and about 20 to 24 percent sodium, by weight, based on the total alkali metal mixture weight. This composition is most preferred because the alkali metal mixture is liquid at room temperature (25° C.), thereby minimizing processing and handling problems.

While the proportion of elemental alkali metal or elemental alkali metal mixture to particulate solids can vary appreciably, generally at least about one weight percent particulate solids, based on total catalyst system weight, will be utilized. Generally, about 10 to 50 weight percent alkali metal, based on total catalyst system weight, is preferred. The most preferred proportion of alkali metal is about 30 to 35 weight percent, based on total catalyst system weight, in order to facilitate flow in tubular reactors and maximize reactant contact with the catalyst system.

The catalyst system, comprising a particulate solid and at least one elemental alkali metal, can be charged directly into a reactor. Such a catalyst system requires no further processing to enable use of the system in the catalysis of a dimerization process.

The catalyst system can be prepared by any method known in the art. The methods of catalyst system preparation include, but are not limited to, the following example. Initially the particulate solids are charged into a container. Then, at least one elemental alkali metal, and optionally a promoter, can be charged to the container while moderately mixing under an inert atmosphere, such as, for example, nitrogen. Then, the catalyst system can be charged to the reactor, under an inert atmosphere. An inert atmosphere is preferred since elemental alkali metals are highly reactive when exposed to moisture or oxygen.

As indicated by the variety of particulate solids, elemental alkali metals, and promoters included within the scope of the invention, numerous combinations are possible to form a catalyst system. Any combination of an elemental alkali metal and optional promoters disclosed can be slurried with any particulate solid disclosed. Some possible combinations are described in detail of the examples which follow. The combination of particulate solid(s), alkali metal(s) and promoter(s) which one may choose to employ will depend on balancing a variety of variables such as for example, reactor configuration, reaction temperature and pressure, olefin feed employed, and rate of olefin feed to obtain desired conversion, selectivity, and isomer ratio.

Reactants

Reactants applicable for use in the process of the invention are olefinic compounds which can (a) dimerize, i.e., self-react, to give useful products, such as the dimerization of propylene to produce 4-methyl-1-pentene; and/or (b) co-dimerize, i.e., react with other olefinic compounds, to give useful products, such as the co-dimerization of ethylene and propylene to produce 1-pentene or the co-dimerization of ethylene and 1-butene to produce 3-methyl-1-pentene. As used herein, the term "dimerization" is intended to include both self-reaction and reaction between olefins, defined as "co-dimerization" above.

Suitable dimerizable olefinic compounds are those compounds having from about 3 to about 30 carbon atoms and having at least one carbon-carbon double bond and at least one allylic hydrogen, i.e., at least one hydrogen atom attached to a carbon atom adjacent to a double-bounded carbon atom. Exemplary compounds include, but are not limited to, acyclic and cyclic olefins such as propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and so forth; 3-methyl-1-butene, 2-methyl-2-butene, 3-methyl-1-pentene, 3-methyl-2-pentene, 4-methyl-1-pentene, 4-methyl-2-pentene, tetramethylethylene, and the like; cyclopentene, cyclohexene, methylcyclopentene, methylcyclohexene, and the like; and mixtures of any two or more thereof.

Suitable co-dimerizable olefinic compounds are those compounds having from 2 to about 30 carbon atoms, including all the compounds contemplated within the scope of the "dimerizable" olefinic compounds as indicated above. In addition, olefinic compounds which do not have at least one allylic hydrogen atom are also included within the scope of co-dimerizable olefins. Exemplary compounds in addition to those indicated above include, but are not limited to, ethylene, 3,3-dimethyl-1-butene, ditertiarybutyl ethylene and the like; and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous types of operations, although the catalyst systems of the invention are particularly well suited for continuous, fixed bed operation. Suitable equipment, such as autoclaves, tubular reactors and the like are well known in the art and can be employed. Due to the corrosive nature of alkali metals, preferred reactor materials of construction include stainless steel, glass-lined reactors, or the like.

The reaction temperature can vary depending on the catalyst system and feed(s) employed. Typically, a temperature range of about 50° to about 500° C. is suitable. Temperatures of about 50° to about 200° C. are preferred with a range of about 80° to about 180° C. most preferred because optimum reaction rates are obtained with minimum by-product formation.

The dimerization reaction can be carried out by contacting the dimerizable olefins with catalyst system in which the olefins are in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 5000 psig and higher are suitable. Preferably, pressures of about 1000 to 3000 psig are employed, with pressures of about 1400 to 1700 psig most preferred in order to achieve a good balance between reaction rate and minimize equipment and operating costs necessitated by very high reaction pressures.

If the reaction is carried out with the olefin reactants in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable solvents or diluents. If the reaction is carried out with the olefin reactants in the gaseous phase, diluents such as aliphatic hydrocarbons, for example methane or ethane and/or substantially inert gases, for example, nitrogen or argon, can be present.

The contact time required for the dimerization reaction depends upon several factors, such as, for example, the activity of the catalyst system, temperature, pressure, structure of the reactants employed, level of conversion desired, and the like. Where the reaction is carried out in continuous fashion, it is convenient to express the reactant to catalyst system contact time in terms of weight hourly space velocity (WHSV), i.e., the ratio of the weight of reactant which comes in contact with a given weight of catalyst system per unit hour, expressed commonly as (grams reactant)/(grams catalyst system)(hour). Thus, a WHSV of about 0.1 to about 10 will be employed. A WHSV of about 0.5 to about 5 is preferred, with about 1 to about 4 most preferred for optimum catalyst productivity.

Products

The olefinic products of the invention have established utility in a wide variety of applications such as for example as monomers for use in the preparation of homopolymers, copolymers, terpolymers, and the like. Such polymers include, but are not limited to, polymethylpentene.

A further understanding of the present invention and its advantages will be provided by reference to the following examples. The examples are provided merely to illustrate the practice of the invention and should not be read as limiting the scope of the invention or the appended claims in any way. Reasonable variations and modifications, not departing from the essence and spirit of the invention, are contemplated to be within the scope of patent protection desired and sought.

EXAMPLES

In each of the following examples, a steam jacketed tubular reactor ($\frac{1}{4}$ inch diameter × 20 inch height) was purged with nitrogen and sealed. The catalyst system was pressure charged through a port at the top of the reactor. Unless otherwise specified, the total charge of the catalyst system was about 25 grams. Propylene feed was bubbled through a 60 micron diameter stainless steel sintered element into the tubular reactor at a 2 ml/min flow rate. The reaction was carried out at about 160° C. and about 1500 psig.

The reaction conditions were evaluated after 8 hours of continuous operation. The conditions were evaluated with respect to propylene conversion, 4-methyl-1-pentene (4MP1) selectivity, and 4-methyl-1-pentene to 4-methyl-2-pentene (4MP2) product isomer ratio.

Propylene conversion is defined as the mass of propylene in a unit volume of feed less the mass of propylene in a unit volume of product, the quantity divided by the mass of propylene in a unit volume of feed, expressed as a percentage. 4MP1 selectivity is defined as the mass of 4MP1 in a unit volume of product divided by the mass of the total unit volume of product, expressed as a percentage. The isomer ratio, 4MP1/4MP2, is defined as the mass of 4MP1 in a unit volume of product divided by the mass of 4MP2 in a unit volume of product, expressed as a percentage.

After 8 hours of reaction time, the reactor effluent was analyzed by gas chromatography. See Table I for a comparison of catalyst systems under similar reaction conditions.

EXAMPLE 1

A commercially available (Callery Chemical Company) eutectic mixture of elemental sodium and elemental potassium was utilized as the elemental alkali metal. This eutectic mixture comprised about 78 weight percent potassium and 22 weight percent sodium, and was liquid at room temperature.

After 8 hours the reaction resulted in 3 percent propylene conversion, 79 percent 4MP1 selectivity, and a 4MP1/4MP2 ratio of 7.

EXAMPLE 2

A 25 gram sample of particulate potassium (Alfa Inorganic Chemicals) was poured into a port in the top of the reactor inside the glove bag under nitrogen. The particulate potassium was converted to molten potassium at the reaction temperature of 160 degrees C.

After 8 hours the reaction resulted in 3 percent propylene conversion, 78 percent 4MP1 selectivity, and a 4MP1/4MP2 ratio of 7.

EXAMPLE 3

A mixture of particulate potassium and glass beads comprised the catalyst system. Approximately 25 grams of this catalyst system was charged to the reactor. The ratio of potassium to glass beads was approximately 1:2 on a weight basis, forming a system containing about ⅓ potassium and about ⅔ glass beads.

After 8 hours the reaction resulted in 7 percent propylene conversion, 82 percent 4MP1 selectivity, and a 4MP1/4MP2 ratio of 8.

EXAMPLE 4

A eutectic mixture of sodium and potassium and 0.25 inch diameter glass beads comprised the catalyst system. The eutectic mixture of sodium and potassium was comprised of about 78 percent potassium and about 22 percent sodium by weight. The ratio of elemental alkali metal mixture to glass beads was about 1:2 on a weight basis, forming a catalyst system having about ⅓ elemental alkali metal mixture and about ⅔ glass beads, based on total catalyst system weight. Approximately 25 grams of this catalyst system was charged to the reactor.

After 8 hours the reaction resulted in 8 percent propylene conversion, 77 percent 4MP1 selectivity, and a 4MP1/4MP2 ratio of 7.

EXAMPLE 5

A mixture of particulate potassium and potassium carbonate (J. T. Baker, <25 mesh) comprised the catalyst system. The ratio of potassium to potassium carbonate was about 1:2 on a weight basis, forming a catalyst system having about ⅓ elemental alkali metal and about ⅔ potassium carbonate, based on total catalyst system weight. Approximately 25 grams of this catalyst mixture was charged to the reactor.

After 8 hours the reaction resulted in 15 percent propylene conversion, 88 percent 4MP1 selectivity, and a 4MP1/4MP2 ratio of 25.

EXAMPLE 6

A eutectic mixture of sodium and potassium and potassium carbonate mixture comprised the catalyst system. The eutectic mixture of sodium and potassium was comprised of about 78 percent potassium and about 22 percent sodium by weight. The ratio of alkali metal mixture to potassium carbonate was about 1:2 on a weight basis, forming a catalyst system having about ⅓ alkali metal mixture and about ⅔ potassium carbonate, based on total catalyst system weight. Approximately 25 grams of this catalyst mixture was charged to the reactor.

After 8 hours the reaction resulted in 11 percent propylene conversion, 88 percent 4MP1 selectivity, and a 4MP1/4MP2 ratio of 26.

EXAMPLE 7

Elemental potassium was supported on an extruded mass of potassium carbonate to form a catalyst system. The potassium carbonate extrudate was prepared from a well-mixed thick paste comprising potassium carbonate and deionized water. The support was dried at about 85° C. for about 2 hours. The support was calcined at 250° C. for 3 hours. After cooling to room temperature, elemental potassium was then added to the support while mixing. The resultant catalyst system comprised approximately 4 percent potassium by weight, based on total catalyst system weight. Approximately 52 grams of this catalyst system was charged to the reactor.

After 8 hours the reaction resulted in 27 percent propylene conversion, 89 percent 4MP1 selectivity, and a 4MP1/4MP2 ratio of 22.

EXAMPLE 8

An extruded mass of sodium and potassium with potassium carbonate comprised the catalyst system. Approximately 52 grams of this catalyst system was charged to the reactor. The catalyst system was comprised of approximately 4% eutectic sodium and potassium by weight, based on total system weight.

After 8 hours the reaction resulted in 14 percent propylene conversion, 79 percent 4MP1 selectivity, and a 4MP1/4MP2 ratio of 9.

TABLE I

| Example | Catalyst | Weight Percent Alkali Metal (Basis: total system) | Propylene Conversion (%) | 4MP1 Selectivity (%) | 4MP1/4MP2 |
|---|---|---|---|---|---|
| 1 | NaK | 100% | 3 | 79 | 7 |
| 2 | K | 100% | 2 | 78 | 7 |
| 3 | K/Glass | 33% | 7 | 82 | 8 |
| 4 | NaK/Glass | 33% | 8 | 77 | 7 |
| 5 | K/K2CO3 | 33% | 15 | 88 | 25 |
| 6 | NaK/K2CO3 | 33% | 11 | 88 | 26 |
| 7 | K/K2CO3 | 4% | 27 | 89 | 22 |
| 8 | NaK/K2CO3 | 4% | 14 | 79 | 9 |

That which is claimed is:

1. A catalyst system composition consisting essentially of:

(a) at least one liquid elemental alkali metal; and
(b) particulate solids; wherein said catalyst system composition is a slurry.

2. A composition according to claim 1, wherein said elemental alkali metal is a mixture of elemental sodium and elemental potassium.

3. A composition according to claim 2, wherein said mixture of elemental sodium and elemental potassium is a liquid at about 25° C. and 1 atmosphere.

4. A composition according to claim 2, wherein said mixture of elemental sodium and elemental potassium is a mixture having greater than about 60 weight percent elemental potassium and less than about 40 weight percent elemental sodium, based on the total weight of the catalyst system.

5. A composition according to claim 2, wherein said mixture of elemental sodium and elemental potassium is a mixture having about 76 to about 80 weight percent elemental potassium and about 20 to about 24 weight percent elemental sodium, based on the total weight of the catalyst system.

6. A composition according to claim 1, wherein said elemental alkali metal is potassium.

7. A composition according to claim 1, wherein said catalyst system further consists essentially of a promoter.

8. A composition according to claim 7, wherein said promoter is graphite.

9. A composition according to claim 1, wherein said particulate solids are alkali metal carbonate particulates.

10. A composition according to claim 9, wherein said alkali metal carbonate is selected from the group consisting of sodium carbonate and potassium carbonate.

11. A composition according to claim 10, wherein said alkali metal carbonate is potassium carbonate.

12. A composition according to claim 1, wherein said particulate solids have a particle size of less than about 0.25 inch diameter.

13. A composition according to claim 2, wherein said mixture of elemental sodium and potassium represents about 10 to about 50 weight percent of said catalyst system.

14. A composition according to claim 2, wherein said mixture of elemental sodium and potassium represents about 30 to about 35 weight percent of said catalyst system.

* * * * *